United States Patent
Samukov et al.

(10) Patent No.: US 6,265,590 B1
(45) Date of Patent: Jul. 24, 2001

(54) $N_\alpha$-2-(4-NITROPHENYLSULFONYL) ETHOXYCARBONYL-AMINO ACIDS

(75) Inventors: Vladimir V. Samukov; Aydar N. Sabirov; Pavel I. Pozdnyakov, all of Novosibirsk (RU); Hack-Joo Kim, Seoul; Young-Deug Kim, Kyungkido, both of (KR)

(73) Assignee: Hyundai Pharm, Ind. Co., Ltd., Seoul (KR)

( * ) Notice: Subject to any disclaimer, the term of this patent is extended or adjusted under 35 U.S.C. 154(b) by 0 days.

(21) Appl. No.: 09/284,732

(22) PCT Filed: Oct. 19, 1996

(86) PCT No.: PCT/KR96/00179

§ 371 Date: Jul. 12, 1999

§ 102(e) Date: Jul. 12, 1999

(87) PCT Pub. No.: WO98/17638

PCT Pub. Date: Apr. 30, 1998

(51) Int. Cl.[7] ............ C07D 233/54; C07C 321/06; C07C 271/10; C07C 271/14; C07C 271/20
(52) U.S. Cl. ............ 548/338.5; 560/13; 560/16; 560/27; 560/29; 560/159; 560/160
(58) Field of Search .................. 560/29, 160, 16, 560/27, 13, 159; 548/338.5

(56) References Cited

FOREIGN PATENT DOCUMENTS 9625394   8/1996   (WO).

OTHER PUBLICATIONS

Chemical Abstracts, vol. 122, No. 7, Feb. 13, 1995 p. 1164. Database CAPLUS on STN, Acc. No. 1995:141534, Samukov et al., '2–(4–nitrophenyl)sulfonylethoxycarbonyl (Nsc) group as a base–labile alpha amino protection for solid peptide synthesis.' Tetrahedron Lett. (1994), 35(42), pp. 7821–4 (abstract), 1995.*

* cited by examiner

*Primary Examiner*—Sreeni Padmanabhan
*Assistant Examiner*—Brian J. Davis
(74) *Attorney, Agent, or Firm*—Birch, Stewart, Kolasch & Birch LLP

(57) ABSTRACT

Protected amino acid derivatives of general formula (I)

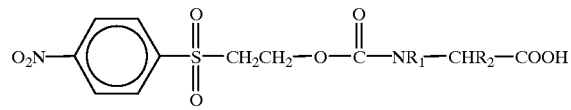

and methods for the prepatation of the derivatives are provided.

6 Claims, No Drawings

$N_\alpha$-2-(4-NITROPHENYLSULFONYL) ETHOXYCARBONYL-AMINO ACIDS

This application is the national phase under 35 U.S.C. §371 of PCT International Application No. PCT/KR96/00179 which has an International filing date of Oct. 19, 1996 which designated the United States of America.

BACKGROUND OF THE INVENTION

The field of the invention concerns new protected amino acid derivatives useful for peptide synthesis, namely, $N_\alpha$-2-(4-nitrophenylsulfonyl)ethoxycarbonyl-amino acids having the general formula I:

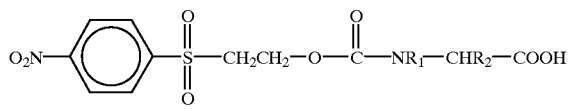

wherein $R_1$ represents a hydrogen atom, and $R_2$ may represent hydroxymethyl, 1-hydroxyethyl, 4-hydroxybenzyl, imidazolyl-2-methyl, benzyloxymethyl, 1-benzyloxyethyl, 4-benzyloxybenzyl, benzyloxycarbonylmethyl, 2-(benzyloxycarbonyl)ethyl, S-benzylthiomethyl, S-(diphenylmethyl)thiomethyl, 4-(benzyloxycarbamido)butyl, 3-guanidinopropyl, 3-$N^G$-toluenesulfonyl) guanidinopropyl, 3-($N^G$-nitro) guanidinopropyl, 3-[$N^G$-(4-methoxy-2,3,6-trimethylbenzenesulfonyl)]-guanidinopropyl, N-(4,4'-dimethoxybenzhydryl)carboxamidomethyl, 2-[N-(4,4'-dimethoxybenzhydryl) carboxamido]ethyl, S-tert-butyldithiomethyl, 4-[2-(4-nitrophenylsulfonyl) ethoxycarbamicdo]-butyl, propyl, butyl, ethyl, 3-(benzyloxycarbamido)propyl, or 3-(tert-butoxycarbamido)propyl, and methods for the preparation thereof.

$N_{60}$ -2-(4-Nitrophenylsulfonyl) ethoxycarbonyl-amino acids (Nsc-amino acids) I represent a class of protected amino acid derivatives which are used in the chemical synthesis of peptides. In these derivatives, $N_\alpha$-2-(4-nitrophenylsulfonyl) -ethoxycarbonyl (Nsc) group serves as a temporary $N_\alpha$-protection which can be selectively removed after each step of the peptide chain elongation. Nsc-Group is fairly resistant to acidic reagents and is cleaved according to the β-elimination mechanism by organic bases in aprotic solvents. Mild conditions of the cleavage allow for use of the temporary $N_\alpha$-Nsc-protection in the peptide synthesis together with the acid-sensitive side chain protection of widely used t-butyl or benzyl type, thus providing the so-called "orthogonality" of the synthetic strategy.

Recently $N_\alpha$-Nsc-amino acids, methods for their preparation, and their employment for the solid phase peptids synthesis have been disclosed in International Publication No. WO96/25394. However, only a minimal set of $N_\alpha$-Nsc-derivatives of proteogenic amino acids has been described, which is intended for the solid phase peptide synthesis with full side-chain protection of acid-labile tert-butyl or compatible type.

SUMMARY OF THE INVENTION

It is, therefore, desirable to develop new $N_\alpha$-Nsc-amino acids to extend the list of derivatives available for solid phase synthesis. On the other hand, it is useful to provide $N_\alpha$-Nsc-amino acid derivatives with another type of side protection (e.g., benzyl of compatible) or without side protection which may give new opportunities for liquid phase peptide synthesis.

An object of the present invention is to provide new $N_\alpha$-Nsc-amino acids derivatives, more particularly, $N_\alpha$-2-(nitrophenylsulfonyl)ethoxycarbonyl-amino acids having the general formula I:

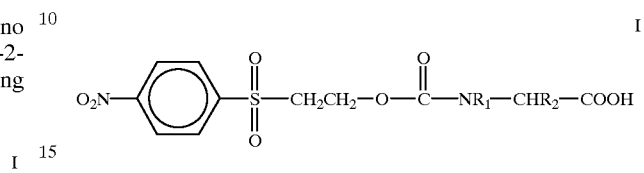

wherein $R_1$ represents hydrogen atom, and $R_2$ may represent a hydroxymethyl, 1-hydroxyethyl, 4-hydroxybenzyl, imidazolyl-2-methyl, benzyloxymethyl, 1-benzyloxyethyl, 4-benzyloxybenzyl, benzyloxycarbonylmethyl, 2-(benzyloxycarbonyl) ethyl, S-benzylthiomethyl, S-(diphenylmethyl)thiomethyl, 4-(benzyloxycarbamido) butyl, 3-guanidinopropyl, 3- ($N^G$-toluenesulfonyl) guanidinopropyl, 3-($N^G$-nitro) guanidinopropyl, 3-[$N^G$-(4-methoxy-2,3,6-trimethylbenzenesulfonyl)]-guanidinopropyl, N-(4,4'dimethoxybenzhydryl) carboxamidomethyl, 2-[N-(4,4'-dimethoxybenzhydryl) carboxamido]ethyl, S-tert-butyldithiomethyl, 4-[(2-(4-nitrophenylsulfonyl)ethoxycarbamido]-butyl, propyl, butyl, ethyl, 3-(benzyloxycarbamido)propyl, or 3-(tert-butoxycarbamido)propyl, which can be employed as $N_\alpha$-protected amino acid derivatives in peptide synthesis.

Another object of the present invention is to provide methods for the preparation of said $N_\alpha$-Nsc-amino acids. These and other objects of the present invention will be apparent from the following description

DETAILED DESCRIPTION OF THE INVENTION $N_\alpha$-Nsc-amino acids (I) of the present invention can be prepared by the treatment of amino acids of the general formula II, wherein $R_1$ and $R_2$ represent the definitions meanings given for formula I, with 2-(4-nitrophenylsulfonyl)ethylchloroformate III in mixed aqueous/organic solvent in the presence of a base and at a temperature of from 0 to 40° C., preferably from 0 to 20° C. (Scheme 1).

Scheme 1

HNR$_1$—CHR$_2$—COOH +

II

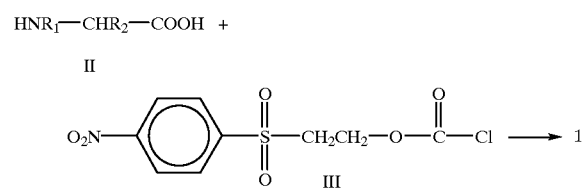

Chloroformate III is introduced into the reaction in amounts of from 0.5 to 1.5 molar equivalents, preferably from 0.7 to 0.9, as related to the amino acid. As an organic component of the solvent any aprotic organic solvent may be used which is capable of dissolving the acylating reagent and is mixible with water, for example, acetonitrile, DMF, tetrahydrofuran or dioxane. A base may be an organic or inorganic base, for example, sodium or potassium carbonate, magnesium or calcium oxide, triethylamine, or N-methylmorpholine.

According to another method of the present invention, amino acids of the general formula II are firstly converted into N,O-trimethylsilyl dervatives using methods known in the art and then treated with equivalent amount of chloroformate III in anhydrous organic solvent, for example, dichloromethane in the presence of base, for example, tertiary amine. After aqueous hydrolysis of the intermediate acylated trimethylsilyl derivatives desirable $N_\alpha$-Nsc-amino acids I are obtained in a free form.

Derivatives of the formula I, wherein $R_1$ is hydrogen, and $R_2$ represents N-(4,4'-dimethoxybenzhydryl) carboxamidomethyl or 2-[N-(4,4'-dimethoxybenzhydryl)carboxamido] ethyl, may be prepared by the reaction of the known derivatives I, wherein $R_1$ is hydrogen, and $R_2$ represents carboxamidomethyl or 2-(carboxamido)ethyl, with 4,4'-dimethoxybenzhydrol in an organic solvent in the presence of a strong acid. As a solvent, acetic acid may be used, and as a strong acid sulfuric or methanesulfonic acid may be used.

A derivative of the formula I, wherein $R_1$ is hydrogen, and $R_2$ represents 3-guanidinopropyl($N_\alpha$-Nsc-Arg-OH), may be prepared by the reaction of arginine with 2-(4-nitrophenylthio)-ethylchloroformate in water in the presence of sodium bicarbonate, resulting $N_\alpha$-2-(4-nitrophenylthio)ethoxycarbonyl-arginine which is then oxidized into the desired $N_\alpha$-Nsc-arginine with hydrogen peroxide in an organic solvent, for example, ethanol or acetic acid.

A derivative of the formula I, wherein $R_1$ is hydrogen, and $R_2$ represents imidazolyl-2-methyl($N_\alpha$-Nsc-His-OH), may be prepared from $N_\alpha$-Nsc-$N_{im}$-protected histidine derivative by selective deprotection of imidazole ring, for example, by selective acidic detritylation of known $N_\alpha$-Nsc-$N_{im}$-triphenylmethyl-histidine.

It is seen from the molecular formula that the compounds of formula I have an asymmetric α-carbon atom. Because the α-carbon atom does not participate in reactions employed for the preparation of compounds of formula I, the configuration of this chiral center existing in starting amino acids II is retained in the resulting $N_\alpha$-Nsc-derivatives I. Therefore, it is clear that the methods of the present invention can be used for the preparation of $N_\alpha$-Nsc-amino acids I in any chiral form (L or D), as well as racemic compounds, depending on the configuration of the compound II.

The meaning of $R_1$ and $R_2$ substituents in derivatives of the formula I according to the present invention correspond to structures of side chains of known α-amino acids containing or not containing protective groups known in the art (Table 1).

TABLE 1

Meanings of $R_1$ and $R_2$ substituents in compounds I

| No | R1 | R2 | Amino acid | Abbreviation |
|---|---|---|---|---|
| I-1 | H | Hydroxymethyl | Serine | Nsc-Ser-OH |
| I-2 | H | 1-Hydroxyethyl | Threonine | Nsc-Thr-OH |
| I-3 | H | 4-Hydroxybenzyl | Tyrosine | Nsc-Tyr-OH |
| I-4 | H | Imidazolyl-2-methyl | Histidine | Nsc-His-OH |
| I-5 | H | Benzyloxymethyl | O-Benzyl-serine | Nsc-Ser(Bzl)-OH |
| I-6 | H | 1-Benzyloxyethyl | O-Benzyl-threonine | Nsc-Thr(Bzl)-OH |
| I-7 | H | 4-Benzyloxybenzyl | O-Benzyl-tyrosine | Nsc-Tyr(Bzl)-OH |
| I-8 | H | Benzyloxycarbonylmethyl | Aspartic acid β-benzyl-ester | Nsc-Asp(OBzl)-OH |

TABLE 1-continued

Meanings of $R_1$ and $R_2$ substituents in compounds I

| No | R1 | R2 | Amino acid | Abbreviation |
|---|---|---|---|---|
| I-9 | H | 2-(Benzyloxycarbonyl)ethyl | Glutamic acid γ-benzyl-ester | Nsc-Glu(OBzl)-OH |
| I-10 | H | S-Benzylthiomethyl | S-Benzyl-cysteine | Nsc-Cys(Bzl)-OH |
| I-11 | H | S-Diphenylmethyl)thiomethyl | S-Diphenylmethyl-cysteine | Nsc-Cys(Dpm)-OH |
| I-12 | H | 4-Benzyloxycarbamido)-butyl | Nε-Benzyloxycarbonyl-lysine | Nsc-Lys(Z)-OH |
| I-13 | H | 3-Guanidinopropyl | Arginine | Nsc-Arg-OH |
| I-14 | H | 3-($N^G$-Toluenesulfonyl)guanidinopropyl | $N^G$-Toluenesulfonyl-arginine | Nsc-Arg(Tos)-OH |
| I-15 | H | 3-($N^G$-Nitro)guanidinopropyl | $NO^G$-Nitro-arginine | Nsc-Arg($NO_2$)—OH |
| I-16 | H | 3-[$N^G$-(4-Methoxy-2,3,6-trimethyl-benzenesulfonyl)] guandinopropyl | $N^G$-(4-Methoxy-2,3,6-trimethyl-benzenesulfonyl)-arginine | Nsc-Arg(Mtr)-OH |
| I-17 | H | N-(4,4'-Dimethoxybenzhydryl)carboxamidomethyl | Nβ-(4,4'-Dimethoxybenzhydryl)-asparagine | Nsc-Asn(Mbh)-OH |
| I-18 | H | 2-[n-(4,4'-Dimethoxybenzhydryl)carboxamido]ethyl | Nγ-(4,4'-Dimethoxybenzhydryl)-glutamine | Nsc-Gln(Mbh)-OH |
| I-19 | H | S-tert-Butyl-dithiomethyl | S-tert-Butylthio-cysteine | Nsc-Cys(StBu)-OH |
| I-20 | H | 4-[2-(4-Nitrophenylsulfonyl)ethoxycarbamido]butyl | Nε-[2-(4-Nitrophenylsulfonyl)-ethoxy carbonyl]-lysine | Nsc-Lys(Nsc)-OH |
| I-21 | H | Propyl | Norvaline | Nsc-Nva-OH |
| I-22 | H | Butyl | Norleucine | Nsc-Nle-OH |
| I-23 | H | Ethyl | α-Aminobutyric acid | Nsc-Abu-OH |
| I-24 | H | 3-(benzyloxycarbamido)-propyl | Nδ-Benzyloxycarbonyl-omitine | Nsc-Om(Z)-OH |
| I-25 | H | 3-(tert-Butoxycarbamido)-propyl | Nδ-tert-Butoxycarbonyl-omitine | Nsc-Om(Boc)-OH |

Together with $N_\alpha$-Nsc-amino acids disclosed in International Publication No. WO96/25394, the compounds of the formula I shown in Table 1 may be used to implement a wide variety of tactical approaches to the peptide synthesis, including not only solid phase but also solution syntheses. Using $N_\alpha$-Nsc-protection it is now possible to develop synthetic schemes of peptide assembly in solution on the basis of tert-butyl type or benzyl type or a mixed type of side-chain protection, and also to apply minimal side-chain protection tactics.

The present invention, therefore, is regarded as an addition to, and a continuation of, aforementioned International Publication No. WO96/25394.

The invention will now be described by way of examples which are provided as an illustration and are not intended as being limiting. All of the amino acids in the following description have L-configuration unless otherwise indicated.

EXAMPLE 1

$N_\alpha$-Nsc-O-Benzyl-Tyrosine (I-7)

8.15 g of O-benzyl-tyrosine and 7.7 g of potassium carbonate were dissolved in 150 ml of water-dioxane mixture (3:1, v/v) and cooled in an ice bath, then a solution of 7.5 g of 2-(4-nitrophenylsulfonyl)ethyl chloroformate III in 70 ml of dioxane was added dropwise within 15 min with stirring. The cooling bath was removed and the mixture was stirred for an additional 20 min, then evaporated to ca. 100 ml under reduced pressure and transferred into a separating funnel. 100 ml of water was added, and the resulting solution was extracted with 2×50 ml of ethyl acetate. The aqueous layer was separated, acidified to pH 2 with 40% sulfuric acid with cooling in an ice bath, then extracted with 3×80 ml of ethyl acetate. Combined extracts were dried over anhydrous sodium sulfate and evaporated at reduced pressure. Recrystallization of the residue from ethyl acetate-hexane gave the desired product I-7 in a form of white crystalline powder (70%). For characterization see Table 2 (Example 7).

EXAMPLE 2

$N_\alpha$-Nsc-Threonine (I-2)

3.58 g of threonine and 100 ml anhydrous dichloromethane were placed into 250 ml round-bottom flask equipped with a reflux condenser and dropping funnel. To the suspension, 9.7 ml of chlorotrimethylsilane was added with vigorous stirring, and the mixture was heated to boiling for 1 hr. The resulting solution was cooled in an ice bath, then 9.0 ml of triethylamine and 9.0 g of chloroformate III were added with stirring. The mixture was stirred for 20 min in an ice bath, then for an additional 1.5 hr at room temperature. The solvent was evaporated at reduced pressure, and the residue was distributed between 200 ml of ethyl acetate and 250 ml of 2.5% aqueous sodium bicarbonate. The aqueous layer was separated, washed with 50 ml of ether, acidified to pH 2 with 1 N hydrochloric acid, then extracted with 3×70 ml of ethyl acetate. The combined extracts were dried with anhydrous sodium sulfate and evaporated at reduced pressure. Trituration of the residue with petroleum ether gave the desired product I-2 in a form of white powder (75%). For characterization see Table 2 (Example 7).

EXAMPLE 3

$N_\alpha$-Nsc-$N_\delta$-Benzyloxycarbonyl-Ornitine (I-24)

8.0 g of $N_{67}$-benzyloxycarbonyl-ornitine and 120 ml of anhydrous dichloromethane were placed into 250 ml round-bottom flask equipped with a reflux condenser and dropping funnel. To the mixture, 12.7 ml of triethylamine and then 7 ml of chlorotrimethylsilane were added with vigorous stirring, and the mixture was heated to boiling for 1.5 hr. The reaction mixture was then cooled in an ice bath, 9.0 g of chloroformate III was added at once, and stirring was continued for 1.5 hr at room temperature. The solvent was evaporated at reduced pressure, and the residue was distributed between 250 ml of ethyl acetate and 250 ml of 2.5% aqueous sodium bicarbonate. The aqueous layer was separated, washed with 50 ml of ether, acidified to pH 2 with 1 N hydrochloric acid, then extracted with 2×100 ml of ethyl acetate. The combined extracts were dried with anhydrous sodium sulfate and evaporated at reduced pressure. Recrystallization of the residue from ethyl acetate-hexane gave the desired product I-24 in a form of white powder (84%). For characterization see Table 2 (Example 7).

EXAMPLE 4

$N_\alpha$-Nsc-N(4,4'-Dimethoxybenzhydryl)-Asparagine (I-17)

3.89 g of $N_\alpha$-Nsc-asparagine and 2.6 g of 4,4'-dimethoxybenzhydrol were dissolved in 25 ml of glacial acetic acid. To the solution 0.4 ml of methanesulfonic acid was added, and the mixture was allowed to stand overnight at room temperature. The resulting mixture was then poured into 100 ml of ice-cold water with mixing, the formed precipitate was filtered off, washed with water and then with ether. The crude product was dissolved in 10 ml of warm DMF, filtered and reprecipitated with ether. The precipitate was collected by filtration, washed with ether and dried in vacuo yielding the desired compound I-17 as a crystalline power (80%). For characterization see Table 2 (Example 7).

EXAMPLE 5

$N_\alpha$-Nsc-Arginine (I-1 3)

To the solution of 1.7 g of sodium bicarbonate and 4.22 g of arginine hydrochloride in 25 ml of water stirred at room temperature 5.74 g of 2-(4-nitrophenylthio)ethylchloroformate was added in five equal portions during 30 min, then stirring was continued for additional 2 hrs. The mixture was saponified to pH 8.5 with conc. ammonia solution and left for 3 hrs at 4° C. The precipitate formed was collected, washed with ice-cold water, dried on the filter with suction and dissolved in 30 ml of acetic acid. To the solution, 4 ml of 34% hydrogen peroxide was added, and the mixture was left for 30 hrs at room temperature. Then the mixture was evaporated to dryness, and the residue was triturated with ethyl acetate, collected by filtration, washed with ether and dried on air to give the desired product I-13(88%). For characterization see Table 2 (Example 7).

EXAMPLE 6

$N_\alpha$-Nsc-Histidine (I-4)

6.6 g of $N_\alpha$-Nsc-$N_{im}$-triphenylmethyl-histidine was dissolved in 30 ml 90% aqueous acetic acid and boiled under reflux for 30 min. After cooling the precipitate was filtered off, and the filtrate was evaporated. The residue was triturated with ether and collected by filtration giving the desired compound I-4 in 95% yield. For characterization see Table 2 (Example 7).

EXAMPLE 7

Properties of $N_\alpha$-Nsc-amino acids I

Shown in Table 2 are the compounds of formula I which were prepared utilizing provided methods described in detail in examples 1–6. Figures in the column "Method" correspond to numbers of examples where particular methods are described. Chromatographic mobility values $R_f$ are shown for thin-layer chromatography sheets Alufolien Keselgel 60 $F_{254}$ (Merck, Darmstadt, Germany); chloroform/methanol/acetic acid, 95:5:3, (A) and benzene/acetone/acetic acid, 100:50:3, (B), were used as developing solvents, spots were detected by UV-absorbance and/or by ninhydrin reaction. Molecular ion masses $(M+H)^+$ were measured using MS-BC-1 time-of-flight mass spectrometer with $Cf^{252}$ radiation-promoted desorption (Electrom SPA, Sumy, Ukraine).

TABLE 2

Properties of $N_\alpha$-Nsc-amino acids I

| Entry 1 | Compound 2 | Method 3 | $R_f$(A) 4 | $R_f$(B) 5 | Molecular formula 6 | Molecular ion, $(M + H)^+$ | |
|---|---|---|---|---|---|---|---|
| | | | | | | Calcd 7 | Found 8 |
| I-1 | Nsc-Ser-OH | 2 | 0.40 | 0.30 | $C_{12}H_{14}N_2O_9S$ | 363.32 | 363.6 |
| I-2 | Nsc-Thr-OH | 2 | 0.42 | 0.35 | $C_{13}H_{16}N_2O_9S$ | 377.35 | 377.6 |
| I-3 | Nsc-Tyr-OH | 2 | 0.40 | 0.37 | $C_{18}H_{18}N_2O_9S$ | 439.44 | 439.9 |
| I-4 | Nsc-His-OH | 6 | 0.15 | 0.10 | $C_{15}H_{16}N_4O_8S$ | 413.40 | 413.1 |
| I-5 | Nsc-Ser(Bzl)-OH | 1,3 | 0.70 | 0.55 | $C_{19}H_{20}N_2O_9S$ | 453.46 | 453.8 |
| I-6 | Nsc-Thr(Bzl)-OH | 3 | 0.70 | 0.55 | $C_{20}H_{22}N_2O_9S$ | 467.49 | 467.9 |
| I-7 | Nsc-Tyr(Bzl)-OH | 1,3 | 0.75 | 0.55 | $C_{25}H_{24}N_2O_9S$ | 529.57 | 530.1 |
| I-8 | Nsc-Asp(OBzl)-OH | 3 | 0.60 | 0.45 | $C_{20}H_{20}N_2O_{10}S$ | 481.47 | 480.9 |
| I-9 | Nsc-Asp(OBzl)-OH | 3 | 0.62 | 0.43 | $C_{21}H_{22}N_2O_{10}S$ | 459.50 | 495.1 |
| I-10 | Nsc-Cys(Bzl)-OH | 3 | 0.75 | 0.60 | $C_{19}H_{20}N_2O_8S_2$ | 469.53 | 469.3 |
| I-11 | Nsc-Cys(Dpm)-OH | 1,3 | 0.75 | 0.70 | $C_{25}H_{24}N_2O_8S_2$ | 545.63 | 545.2 |
| I-12 | NsC-Lys(Z)-OH | 3 | 0.65 | 0.50 | $C_{23}H_{27}N_3O_{10}S$ | 538.58 | 538.3 |
| I-13 | Nsc-Arg-OH | 5 | 0.10 | 0.05 | $C_{15}H_{21}N_5O_8S$ | 432.45 | 432.8 |
| I-14 | Nsc-Arg(Tos)-OH | 1,2 | 0.35 | 0.30 | $C_{22}H_{27}N_5O_{10}S_2$ | 586.64 | 586.9 |
| I-15 | Nsc-Arg($NO_2$)—OH | 2 | 0.25 | 0.15 | $C_{15}H_{20}N_6O_{10}S$ | 477.45 | 477.1 |
| I-16 | Nsc-Arg(Mtr)-OH | 3 | 0.43 | 0.35 | $C_{25}H_{33}N_5O_{10}S_2$ | 628.73 | 629.4 |
| I-17 | Nsc-Asn(Mbh)-OH | 4 | 0.55 | 0.38 | $C_{28}H_{29}N_3O_{11}S$ | 616.65 | 616.1 |
| I-18 | Nsc-Gln(Mbh)-OH | 4 | 0.58 | 0.33 | $C_{29}H_{31}N_3O_{11}S$ | 630.68 | 630.2 |
| I-19 | Nsc-Cys(StBu)-OH | 3 | 0.60 | 0.45 | $C_{16}H_{22}N_2O_8S_3$ | 467.57 | 567.2 |
| I-20 | Nsc-Lys(Nsc)-OH | 3 | 0.55 | 0.40 | $C_{24}H_{28}N_4O_{14}S_2$ | 661.66 | 662.1 |
| I-21 | Nsc-Nva-OH | 2 | 0.65 | 0.50 | $C_{14}H_{18}N_2O_8S$ | 375.39 | 375.6 |
| I-22 | Nsc-Nle-OH | 2 | 0.65 | 0.50 | $C_{15}H_{20}N_2O_8S$ | 389.42 | 389.6 |
| I-23 | Nsc-Abu-OH | 2 | 0.60 | 0.47 | $C_{13}H_{16}N_2O_8S$ | 375.40 | 375.8 |
| I-24 | Nsc-Om(Z)-OH | 3 | 0.62 | 0.47 | $C_{22}H_{25}N_3O_{10}S$ | 533.55 | 534.0 |
| I-25 | Nsc-Om(Boc)-OH | 3 | 0.65 | 0.43 | $C_{19}H_{27}N_3O_{10}S$ | 490.53 | 491.0 |

What is claimed is:

1. $N_\alpha$-2-(4-nitrophenylsulfonyl)ethoxycarbonyl-amino acids having the general formula:

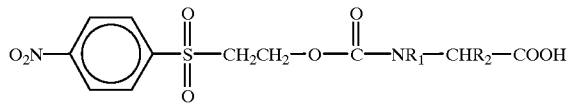

I wherein $R_1$ represents a hydrogen atom, and $R_2$ may represent hydroxymethyl, 1-hydroxyethyl, 4-hydroxybenzyl, imidazolyl-2-methyl, benzyloxymethyl, 1-benzyloxyethyl, 4-benzyloxybenzyl, benzyloxycarbonylmethyl, 2-(benzyloxycarbonyl)ethyl, S-benzylthiomethyl, S-(diphenylmethyl)thiomethyl, 4-(benzyloxycarbamido)butyl, 3-guanidinopropyl, 3-($N^G$-toluenesulfonyl)guanidinopropyl, 3-($N^G$-nitro)guanidinopropyl, 3{$N^G$(4-methoxy-2,3,6-trimethylbenzenesulfonyl)}-guanidinopropyl, N-(4,4'-dimethoxybenzhydryl)carboxamidomethyl, 2-{N-(4,4'-dimethoxybenzhydryl)carboxamido}ethyl, S-tert-butyldithiomethyl, 4-{2-(4-nitrophenylsulfonyl)ethoxycarbamido}-butyl, propyl, butyl, or ethyl.

2. A method for preparing $N_\alpha$-2-(4-nitrophenylsulfonyl) ethoxycarbonyl amino acids according to claim 1 comprising reacting an amino acid of the general formula II

II wherein $R_1$ and $R_2$ are the same as defined in claim 1, with 2-(4-nitrophenylsulfonyl) ethoxycarbonyl chloroformate in a mixed aqueous-organic solvent in the presence of a base.

3. A method for preparing $N_\alpha$-2-(4-nitrophenylsulfonyl) ethoxycarbonyl amino acids according to claim 1 comprising:

a) converting an amino acid of the general formula II

II wherein $R_1$ and $R_2$ are the same as defined in claim 1, into O,N-trimethylsilylated derivatives;

b) reacting said O,N-trimethylsilylated derivatives with 2-(4-nitrophenylsulfonyl) ethoxycarbonyl chloroformate in an aprotic solvent in the presence of a base, followed by hydrolysis.

4. A method for preparing $N_\alpha$-2-(4-nitrophenylsulfonyl) ethoxycarbonyl amino acids according to claim 1 wherein $R_1$ represents a hydrogen atom, and $R_2$ represents N-(4,4'-dimethoxybenzhydryl)carboxamidomethyl or 2-{N-(4,4'-dimethoxybenzhydryl)carboxamido}ethyl, comprising reacting $N_\alpha$-2-(4-nitrophenylsulfonyl)-ethoxycarbonyl-asparagine or $N_\alpha$-2-(4-nitrophenylsulfonyl)-ethoxycarbonyl-glutamine, with 4-4'-dimethoxybenzhydrol in an organic solvent in the presence of an acid.

5. A method for preparing $N_\alpha$-2-(4-nitrophenylsulfonyl) ethoxycarbonyl amino acids according to claim 1, wherein $R_1$ represents a hydrogen atom, and $R_2$ represents 3-guanidinopropyl, comprising (a) reacting arginine with 2-(4-nitro-phenylthio) ethyl-chloroformate in water in the presence of sodium bicarbonate; and (b) oxidizing the thus formed $N_\alpha$-2-(4-nitrophenylthio) ethoxycarbonyl-arginine with hydrogen peroxide in an organic solvent.

6. A method for preparing $N_\alpha$-2-(4-nitrophenylsulfonyl) ethoxycarbonyl amino acids according to claim 1 wherein $R_1$ represents a hydrogen atom, and $R_2$ represents imidazole-2-methyl, comprising reacting $N_\alpha$-2-(4-nitrophenylsulfonyl)-ethoxycarbonyl-$N_{im}$-triphenylmethyl-histidine with acid.

* * * * *